United States Patent [19]

Sagiv et al.

[11] Patent Number: 4,964,972
[45] Date of Patent: Oct. 23, 1990

[54] IONIC RECOGNITION AND SELECTIVE RESPONSE IN SELF ASSEMBLING MONOLAYER MEMBRANES ON ELECTRODES

[75] Inventors: Jacob Sagiv, Ness Ziona; Israel Rubinstein, Rishon-le-Zion; Suzi Steinberg, Rehovot; Abraham Shanzer, Rehovot; Yitzhak Tor, Rehovot, all of Israel

[73] Assignee: Yeda Research and Development Company Limited, Rehovot, Israel

[21] Appl. No.: 330,508

[22] Filed: Mar. 30, 1989

[51] Int. Cl.$^5$ ............................................. G01N 27/333
[52] U.S. Cl. ............................... 204/418; 204/56.1; 427/58
[58] Field of Search ................. 204/418, 56.1; 427/58

[56] References Cited

U.S. PATENT DOCUMENTS 4,637,861 1/1987 Krull et al. .................... 204/1 T
4,661,235 4/1987 Krull et al. .................... 204/414

Primary Examiner—G. L. Kaplan
Attorney, Agent, or Firm—Browdy and Neimark

[57] ABSTRACT

According to the invention organic monolayer films are applied to an electrically conductive substrate, resulting in an electrode which can be used in electrochemical processes. The said film serves as ultrathin membrane and allows certain selected species to approach the substrate and be detected. The film comprises active species which are selective towards specific species contained in mixture with others and a blocking surface sealing component. It is also possible to use one compound serving both purposes. The components of the film are attached to the substrate by a variety of means: adsorption, chemisorption, electro-chemical deposition.

11 Claims, 3 Drawing Sheets

IONIC RECOGNITION AND SELECTIVE RESPONSE IN SELF ASSEMBLING MONOLAYER MEMBRANES ON ELECTRODES

FIELD OF THE INVENTION:

There are provided selective electrodes for use in electrochemical sensing devices. There is provided a method for the production of such electrodes. The novel selective electrodes are characterized by a surface layer, generally an organic monolayer comprising an inert monolayer matrix in which there are embedded synthetic "receptor sites" adapted to provide species selectivity. The inert matrix blocks vacant sites on the surface and thus prevents the approach of undesired species to the surface of the electrode. The electrode is made of an electrically conducting substance, to which the monolayers including the inert and active species of the monolayer is bonded.

BACKGROUND OF THE INVENTION:

Impermeable one-molecule thick barriers for ions and water have been produced on gold, using techniques of monlayer self-assembly (Sabatani et al., J. Phys. Chem. 91 6663-9 (1987)).

To confer ion-specificity to a metal electrode, the mere binding of ion-specific molecules to the electrode surface is not enough, as there must be prevented leakage of other, undesired species which might react electrochemically at the electrode.

SUMMARY OF THE INVENTION:

There is provided an electrode, made of a non-specific electrically conductive material, coated with a stable ion-selective monolayer which, in certain aspects, is similar in performance to basic structural and functional principles of natural bilayer membranes. The process of the invention is based on the self-assembly of such monolayer structures. The essentially monolayer surface coatings applied to non specific conductive substrates comprise an inert molecular matrix in which there is embedded a second component, providing specific synthetic receptor sites. In particular cases it is possible to produce the surface layer from a substance which fulfills both such functions. The monolayer-coated electrodes of the invention are capable of recognizing selected species out of a mixture of a variety of species. They are especially suited to recognize certain ionic species in a system containing such species in a mixture with other, otherwise interfering species. The inert matrix prevents interference of such undesired species by preventing their access to the immediate vicinity of the electrode surface.

The invention also relates, as pointed out above, to a process for the production of such selective monolayers and electrodes coated therewith. The invention also relates to the use of such electrodes in electrochemical sensing devices and to assays based on the use of such electrodes. The invention relates to the deposition of organic films of molecular thickness (monolayers) on a suitable electrically conducting solid surface to be used as electrode in an electrochemical process, which organic film functions as a selective ultrathin membrane conferring chemical selectivity (specific responses) to the electrode in a selected electrochemical process.

The chemical selectivity of the monolayer membranes of the present invention is a consequence of their double function as:

a) Dense molecular barriers efficiently blocking passage to the electrode of undesired chemical species from a fluid phase contacting the electrode;

b) Specific receptors for certain chemical species in the fluid phase, for which electrochemical detection at the electrode is required.

Monolayer membranes providing such double function capability are, in general, made of one or more molecular components, at least one of which (the "specific receptor" component) displays binding and/or permeation specificity towards one or more selected species in the fluid phase, and, at least one of which (the "blocking" component) prevents undesired species from the fluid phase from approaching the electrode surface to a distance at which their electrochemical detection by the electrodes will occur. It is also possible to use only one component which provides both membrane functions, i.e. that of the specific receptor for certain selected species, and that of an efficient blocking barrier for other, undesired species.

As specific receptor components there can be used any molecule which can be incorporated in a solid-supported monolayer and which is capable of allowing the passage of certain selected chemical species to the electrode, or which can immobilize certain such species at a distance from the electrode surface that is sufficiently small to permit measurable exchange of electrical charge with the electrode and thus detection of electrochemical activity. Suitable receptor components may be, for example, molecules which, when incorporated in a stable monolayer on the electrode surface, can bind selected ions or molecules from solution through complex formation, or are provided with well defined molecular-size channels through which such selected species from solution may diffuse to the electrode. Blocking components are molecules which can be part of a solid-supported monolayer and which fill free spaces (pinholes) in the monolayer membrane, including molecular-size pinholes, while providing a sufficiently thick and compact layer through which species from the fluid phase that are not "recognized" by the receptor component cannot diffuse to the electrode surface or approach it to a distance at which measurable exchange of electrical charge with the electrode will be detected. The fluid phase may be any liquid, gas, solution in a liquid or in a gas, or any viscous liquid, solid material, or solution in such materials, which can contain mobile chemical species that are electrochemically active and may thus participate in, or affect electrochemical processes. As chemical species in the fluid phase one may consider any molecule or ion, organic, inorganic, or of biological origin, which may undergo or affect any electrochemical process at an electrode surface, and, thus, may be detected electrochemically through such process. For the deposition of monolayer membranes on solid electrode surfaces, of the type pertinent to the present invention, one can use processes such as adsorption, chemisorption, or electrochemical deposition of the membrane components from any suitable organic or aqueous solution, from a gaseous phase, or from the melt of the membrane components. The membrane components may be deposited on the electrode surface simultaneously or sequentially. A compound fulfilling both functions can be used.

EXAMPLE 1

The invention is illustrated with reference to the enclosed figures, in which.

Figure 1:
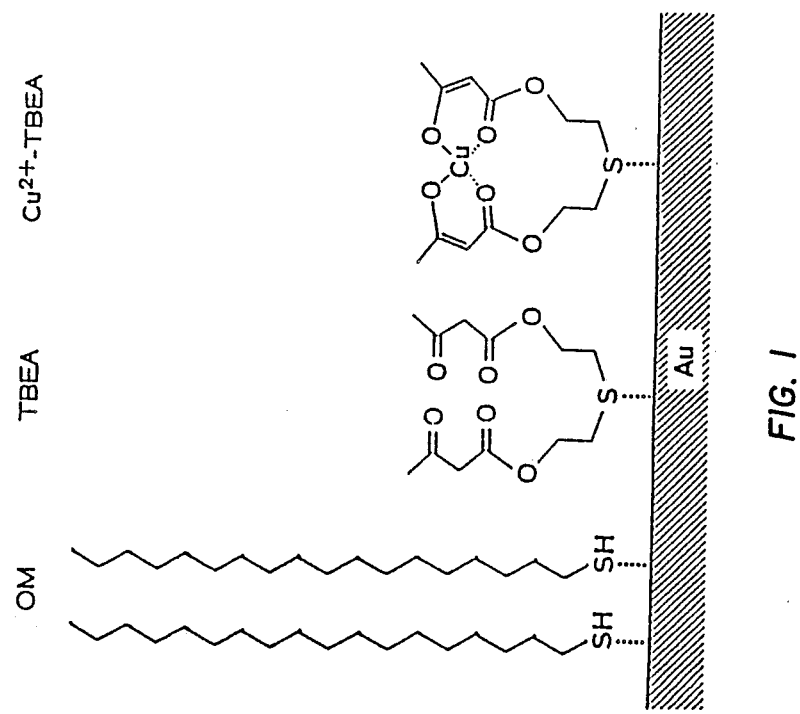
FIG. 1 is a schematic representation of TBEA, TBEA-copper complex and octadecyl mercaptan.

We show here the feasibility of an approach based upon the use of self-assembled mixed monolayers, containing both "active" (monolayer-forming ligand) and "blocking" (surface-sealing long-chain amphiphile) components, so that a specific response for metal ions forming 1:1 complexes with the ligand is achieved. An example relates to the ligand 2,2'-thiobisethyl acetoacetate, $S(CH_2CH_2OCOCH_2COCH_3)_2$ (TBEA, FIG. 1) designed and synthesized as "active" component. The two $\beta$-keto ester groups of TBEA form a tetradentate chelating centre, and the sulphur bridge was designed to anchor the ligand to a gold surface. Surface-bound tetradentate TBEA is an excellent candidate for the formation of 1:1 complexes with divalent metal ions, such as $Cu^{2+}$, but is geometrically unsuited for binding trivalent metal ions, such as $Fe^{3+}$, that require octahedral coordination. Therefore, in terms of geometric discrimination (and also electrochemical suitability), $Cu^{2+}$ and $Fe^{3+}$ are convenient ionic probes to test the selectivty of the monolayer-coated electrodes.

FIG. 2a shows a cyclic voltammogram of a bare gold electrode in $H_2SO_4$ solution containing $Cu^{2+}$ and $Fe^{3+}$. The $Fe^{3+/2+}$ reduction-oxidation peaks are marked with arrows; the small peaks around $-0.15$ V correspond to underpotential deposition (UPD) of a monolayer of Cu on Au and the peaks at $-0.55$ V (reduction) and $-0.40$ V (oxidation) correspond to deposition-dissolution of bulk Cu. Examination of an electrode coated with only TBEA (FIG. 2b) indicates a film structure not sufficiently compact to prevent leakage of $Fe^{3+}$ through uncovered portions of the electrode. TBEA was adsorbed on gold by immersion in a solution containing $3.3 \times 10^{-2}$ M TBEA in bicyclohexyl:chloroform, 4:1 v/v, for 3.5 h; the resulting electrodes are denoted Au/TBEA. Evidently the introduction of an appropriate "blocking" element is necessary for the proper functioning of the system. It was expected that addition of a surface-sealing monolayer component to the adsorption solution might result in a continuous mixed monolayer barrier with ion-selective sites embedded within a compact, electrochemically inert matrix. Previous experience pointed to n-octadecyl mercaptan, $CH_3(CH_2)_{17}SH$ (OM, FIG. 1) as a suitable such component. Thus mixed monolayer mebranes were prepared on gold substrates by co-adsorption of the two components from a solution containing $2.0 \times 10^{-2}$ M TBEA + $2.0 \times 10^{-2}$ M OM in bicyclohexyl:chloroform, 4:1 v/v, for 3.5 h. These electrodes are denoted Au/(TBEA+OM).

The performance of the mixed (TBEA+OM) monolayer membranes was compared with that of gold electrodes coated with the same ligand, but sealed with a thin electrodeposited polymeric film ($\sim$ 10–15 Å thick) of 1-naphtol (NP), known to suppress electrochemical reactivity (FIG. 2c). FIG. 2e and f show, respectively, voltammetric curves of an Au/(TBEA +NP) electrode in $Cu^{2+}$ solution and in a mixed solution of $Cu^{2+}$ and $Fe^{3+}$. Although the electrode is inert to $Fe^{3+}$, $Cu^{2+}$ peaks are clearly observed. The voltammogram of the soluble $Fe^{3+}$-ethylacetoacetate complex in FIG. 2i indicates that the absence of $Fe^{3+/2+}$ peaks in FIG. 2c and f is not due to a possible shift in the redox potentials of complexed $Fe^{3+}$.

The qualitative behaviour of a typical Au/(TBEA+OM) electrode, shown in FIG. 2d and g for solutions containing $Fe^{3+}$ or both $Cu^{2+0}$ and $Fe^{3+}$ions, respectively, is similar to that of Au/(TBEA +NP) (FIG. 2c and f); however, a considerably decreased background, virtually coinciding with the baseline, in FIG. 2d and g, indicates a clear improvement of the barrier properties for the mixed monolayer membrane. Thus the selective complexation of $Cu^{2+}$ enables its penetration into the monolayer and electron exchange with the underlying electrode, whereas hydrated $Fe^{3+}$ remains in the bulk solution at considerably greater distance from the electrode, which precludes its electrochemical reduction in the applied voltage range. $Fe^{3+}$ forms a red complex with dissolved TBEA, possibly an oligomeric octahedral complex. For steric reasons, this should be prevented when the ligand is bound to the surface in an oriented monolayer. Total suppression of voltammetric response is also observed with other ions, which are either trivalent (for instance, $Ce^{3+}$) or sterically incompatible (for instance, $VO^{2+}$). The monolayers on gold were characterized by contact-angle measurements, reflection-absorption Fourier tranform infrared (RA-FTIR) spectroscopy, and various electrochemical measurements. Indirect electrochemical evidence indicates $\sim$50% ligand coverage in the present (TBEA+OM) mixed monolayers. Surprisingly high contact angles for Au/(TBEA +OM), indicative of a rather unusual mode of film packing (typical values: 108°, 59° and 57° for water, bicyclohexyl and n-hexadecane, respectively, with no hysteresis) and significant contact angle variations are observed after $Cu^{2+}$ uptake and removal. FIG. 3 shows selected infrared spectra for the Au/(TBEA+OM) system, from which a number of general conclusions can be drawn: (1) complexed TBEA (enol form) can be detected spectroscopically in the monolayer on gold, (2) the enol form is preserved upon electrochemical removal of the $Cu^{2+}$; (3) differences in the relative intensities of the various C-H stretch peaks in FIG. 3a, b and c are indicative of nonrandom orientation of TBEA on the surface; (4) the system appears stable towards electrochemical treatment. Common prominent features in FIG. 2f and g, which may be correlated with structural characteristics of an ordered $Cu^{2+}$-selective monolayer barrier, are: (1) the complete absence of $Fe^{3+/2+}$ peaks; (2) the absence of Cu UPD peaks; (3) the negative shift of the bulk Cu disposition peak by $\sim$0.25 V; (4) the existence of a loop when the voltammetric scan direction is reversed. The absence of Cu UPD peaks may indicate that Cu atoms are deposited inside the organized monolayer at some distance from the surface, not in direct contact with the gold substrate. The shift in the bulk Cu deposition potential and the voltammetric loop are indicative of the preferred perpendicular orientation of the ligand. In a monolayer where TBEA molecules are oriented normal to the substrate plane (as in FIG. 1), the complexed $Cu^{2+}$ ions are held at a distance of $\sim$ 7 Å from the Au surface, which introduces a tunnelling barrier for electron transfer with the underlying electrode (assuming that quantum-mechanical tunnelling governs electron transfer over distances of this order of magnitude). However, reduced Cu atoms are not complexed and may be deposited within the ligand "cavity" closer to the electrode, thus lowering the energy barrier for further electron transfer. Voltammetrically, the initial barrier is manifested as an increased overpotential for the reduction, i.e. a negative shift of the reduction potential, whereas the easier electron transfer provided by the first layer of deposited Cu atoms gives rise to an autocatalytic effect, appearing as an enhanced reduction current (and thus a loop) of the reverse scan. Experiments with decreasing reversal potentials (not shown) indicate that even submonolayer amounts of Cu atoms may cause such appreciable catalytic effects.

From the negative shift of the $Cu^{2+}$ reduction peak potential, observed with Au/(TBEA +OM) relative to a bare gold electrode (FIGS. 2g and i), and considering a tunnelling mechanism for the electron exchange with the metal, one can estimate the potential shifts to be expected for varying distances between $Cu^{2+}$ and the underlying electrode. To verify these expectations, a new ligand molecule which contains an additional methylene group, 3,3'-thiobispropyl acetoacetate, $S(CH_2CH_2CH_2OCOCH_2COCH_3)_2$ (TBPA), was prepared and tested under identical electrochemical conditions. Assuming a similar orientation of the two ligands with respect to the substrate, the metal ion with TBPA should be located 0.5–1.0 Å further away from the gold surface than with TBEA. Indeed, this results in a reduction peak potential more negative by ~0.030 V for the deposition of Cu with TBPA (FIG. 2g and h), which agrees qualitatively with the proposed tunnelling mechanism.

EXAMPLE 2

Under certain conditions one single compound can fulfil both functions, selectivity and blocking. Sputter deposited gold on a glass slide was annealed for 3 h at 250° C. and thus there was produced a gold layer which was smoother by a factor of 2–3 compared with untreated sputter-deposited gold. A TBEA monolayer was absorbed according to the usual procedure and a layer of considerably better quality was obtained. No additional blocking agent was required. When the Au/TBEA was tested electrochemically in the same manner, in a 0.1 M $H_2SO_4$ containing 1.0 mM $Cu^{2+}$ and 3.0 mM $Fe^{3+}$, it displayed the same selectivity as was achieved with mixed monolayers of the other examples on a regular gold substrate.

EXAMPLE 3

Selective behaviour is observed when TBEA is replaced with TBPA or when the blocking agent OM is replaced with naphthol polymer (NP) or polymerizable octadecyl trichlorosilane (OTS). Diffusion-controlled faradaic currents are generally enhanced at randomly distributed pinholes. A situation in which the bulk-copper peaks are prominent whereas copper "under potential" and $Fe^{3+}/Fe^{2+}$ peaks are totally absent would therefore require rather unusual size and spatial distributions of pinholes. Being deposited electrochemically, NP should block all uncoated electrochemically accessible sites. An NP layer of comparable thickness on a bare gold surface indeed blocks copper deposition completely. Ionic competition experiments provide strong experimental support for the selective complexation model. $Zn^{2+}$ and $Cd^{2+}$ ions, which resemble $Cu^{2+}$ in coordination requirements, successfully replace $Cu^{2+}$ at monolayer ligand sites although being electrochemically inactive under the present conditions. The $Cu^{2+}$ peaks are suppressed in the presence of $Zn^{2+}$, and at a high $Zn^{2+}$ concentration (~8.0 mM) the $Cu^{2+}$ peaks cannot be detected at all. The same is observed with $Cd^{2+}$ (in both cases the peaks are fully recovered in pure $Cu^{2+}$ solution). Conversely, the presence of noncomplexing ions, such as $Fe^{3+}$ or $Ce^{3+}$, has essentially no effect on copper deposition. The complete disappearance of $Cu^{2+}$ peaks in these competition experiments indicates the absence of electrochemically active pinholes down to <0.005% of the total area.

LEGENDS TO FIGURES

FIG. 1 is a schematic representation of TBEA, $Cu^{2+}$ - TBEA complex, and n-octadecyl mercaptan (OM), adsorbed on gold substrate. Note that the ligand binds $Cu^{2+}$ in the enol form upon losing two protons, and thus the complex is neutral. TBEA was prepared by the 4-dimethylaminopyridine (DMAP)-catalysed reaction of 2,2'-thiobisethanol with diketene. Gold electrodes were prepared by sputter-deposition of ~1,000 Å gold on glass microscope slides followed by annealing for 15 min at 420° C., which reduces the gold-surface roughness.

Figure 2:
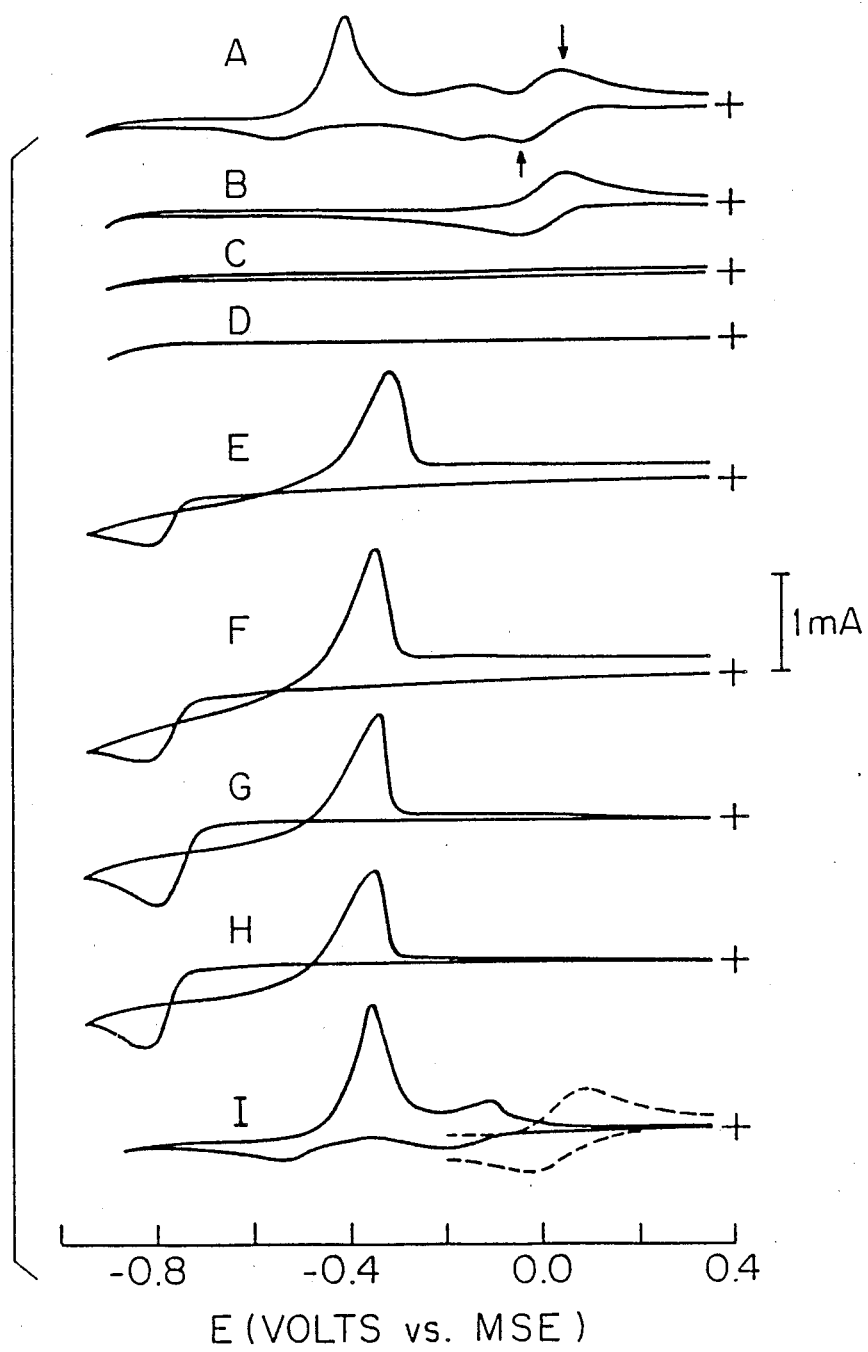
FIG. 2 is a cyclic voltammogram is set out in the Legend to Figures.
Figure 3:
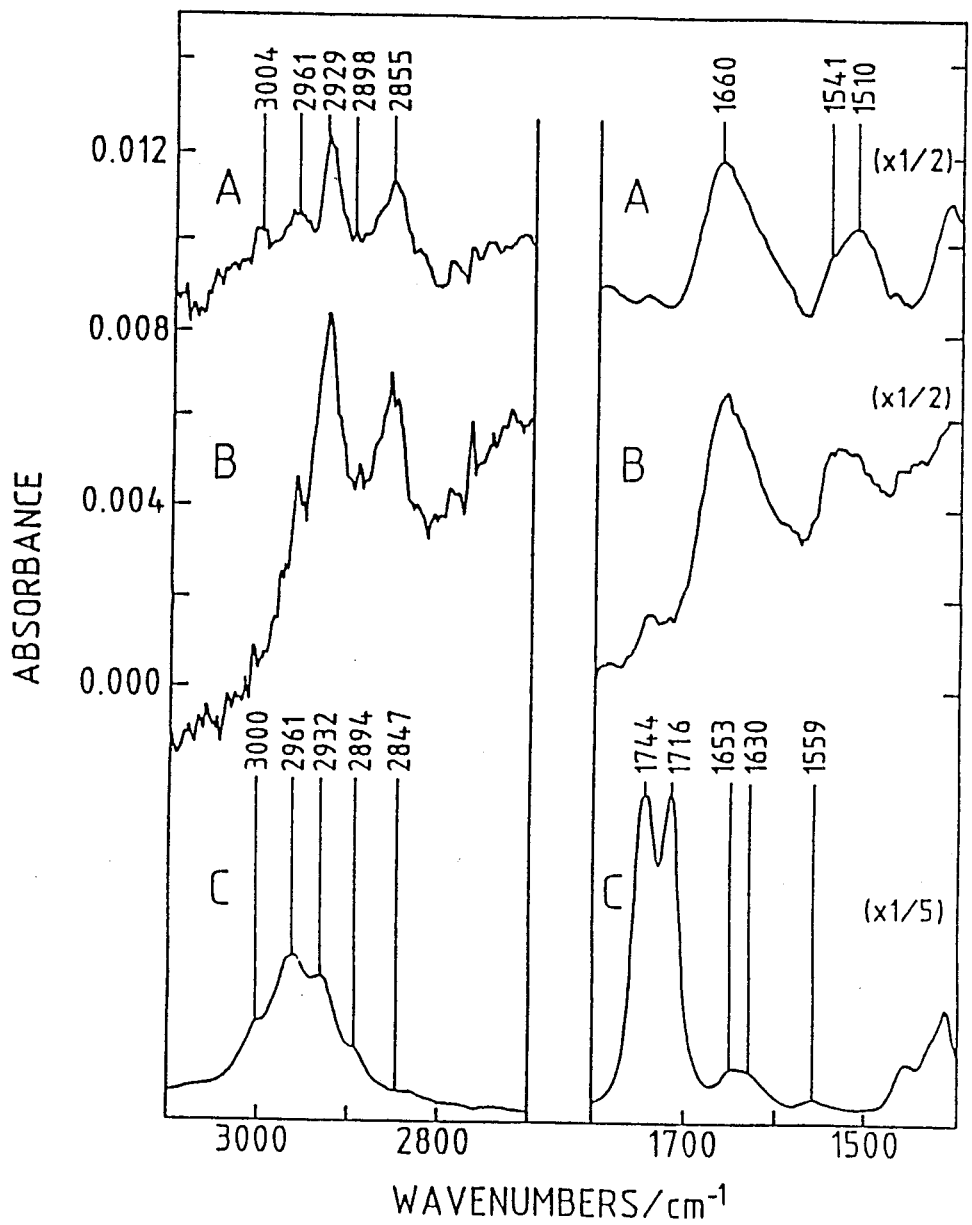
FIG. 3 illustrates RA-FTIR spectra of TBEA complexes with a monolayer structure of the invention.

FIG. 2 presents cyclic voltammograms in 0.1 M $H_2SO_4$ containing 1.0 mM $Cu^{2+}$, 3.0 mM $Fe^{3+}$, or both (scan rate: 0.10 V $s^{-1}$; electrode area: 0.63 $cm^2$; MSE is mercurous sulphate reference electrode, +0.400 V versus saturated calomel electrode). a, Au in $Cu^{2+} + Fe^{3+}$; b, Au/TBEA (~80% coverage) in $Fe^{3+}$; c, Au/(TBEA+NP) in $Fe^{3+}$; d, Au/TBEA+OM) in $Fe^{3+}$; e, Au/(TBEA+NP) in $Cu^{2+}$; f, Au/(TBEA +NP) in $Cu^{2+} + Fe^{3+}$; g, Au/(TBEA+OM) in $Cu^{2+} + Fe^{3+}$; h, Au/(TBPA+OM) in $Cu^{2+} + Fe^{3+}$; i, Au in 0.1 M $H_2SO_4$ containing 0.4 M ethyl acetoacetate and either $Cu^{2+}$ (solid line) or $Fe^{3+}$ (broken line). The ligand coverage was estimated from the minimal amount of charge required to block Au/(TBEA) with naphthol polymer (towards $Fe^{3+}$) compared to that required to block a bare electrode of the same geometric area. Surface coverages of ca. 80% with TBEA are typical. Essentailly the same curves as c and d are obtained, respectively, for Au/NP and Au/OM in either $Cu^{2+}$, $Fe^{3+}$, or $Cu^{2+} + Fe^{3+}$. For c,e,f, naphthol polymer (NP) was deposited in a stirred solution containing 1.0 mM 1-naphthol in 0.5 M $H_2SO_4$ by passing a constant anodic current of 2.0 μA $cm^{-2}$ for 4.5 min. This corresponds to about 10 layers of NP deposited at ligand-uncovered sites of the electrode, which results in a NP film thickness comparable with that of the ligand monolayer itself.

FIG. 3 illustrates RA-FTIR spectra of: a, $Cu^{2+}$ - TBEA complex in a Au/($Cu^2$-TBEA+OM) electrode (specimen obtained by immersion of Au/(TBEA+OM) in saturated aqueous copper acetate solution adjusted to pH 7.5 with sodium acetate, for 1.5 h at 40–45° C.); b, TBEA in the electrode of a, after electrochemical removal of the $Cu^{2+}$ by cycling three times in 0.1 M $H_2SO_4$ between +0.35 V and −0.75 V (v. MSE); c, TBEA in bulk liquid. The spectra in a and b were produced by a weighted subtraction of Au/OM spectrum from the spectra of the respective electrodes in a and b. The spectral features in the 3,000–2,800 $cm^{-1}$ region represent various C-H stretch modes. The peaks at 1,744 and 1,716 $cm^{-1}$ are C=O stretch modes of the ester and ketone functions, respectively, of TBEA in the keto form. The features between 1,660 and 1,510 $cm^{-1}$ are characteristic of the $Cu^{2+}$acetoacetate complex, the bands around 1,660 $cm^{-1}$ (a,b) and 1,653–1,630

$cm^{-1}$ (c) thus being assigned to the conjugated ester and double bond of TBEA in the enol form (see FIG. 1). The spectra in a and b were taken with parallel polarized radiation in the reflection-absorption (RA) mode, at an angle of incidence of 75° and a resolution of 4 $cm^{-1}$. The spectrum in c was taken in the transmission mode, at the same resolution, using a thin film of pure TBEA between two NaCl windows.

We claim:

1. An electrode for use in electrochemical sensing devices wherein said electrode comprises a non specific electrically conducting metal substrate on which there is a self-assembled monolayer which contains an active species specific component and a blocking surface sealing component.

2. An electrode as claimed in claim 1, where the active component and the sealing component are different compounds.

3. An electrode according to claim 1, where the active species and the sealing properties are provided by the same compound.

4. An electrode according to claim 1, where the active species provides selected access to a specific ion out of a mixture of a plurality of ions in solution, to the immediate vicinity of the conductive substrate.

5. An electrode as claimed in claim 1, where the active species is provided by a molecule having at its one end a chemical moiety for anchoring to the electrode conducting substrate, and at its other end a chelate forming group.

6. An electrode according to claim 5, where the active species is selected from 2,2'-thiobisethyl acetoacetate and 3,3'-thiobispropyl acetoacetate to form complexes with ions from solution compounds, and which is embedded in a compact electrochemically inert matrix made of n-octadecyl mercaptan, n-octadecyl trichorosilane, or a naphthol polymer or homologues thereof.

7. An electrode according to claim 5, wherein said active species is a thio acetoacetate substituted with two $\beta$-keto ester groups.

8. An electrode according to claim 5, wherein said active species is a compound forming a tetradentate chelating centre and has a sulphur bridge.

9. An electrode according to claim 1 wherein said self-assembled monolayer is a monolayer applied on said substrate by adsorption, chemisorption or electrochemical deposition.

10. An electrode in accordance with claim 1, wherein said active component and said blocking component are provided in said self-assembled monolayer by adsorption, chemisorption or electrochemical deposition of a compound or compounds supplying said active and blocking components.

11. A process for the production of an electrode for use in an electrochemical sensing device comprising, applying on a surface layer by adsorption, chemisorption or electrochemical deposition, either simultaneously or sequentially, an organic monolayer comprising an inert monolayer matrix in which there is embedded synthetic receptor sites adapted to provide ionic specific selectivity.

* * * * *